(12) United States Patent
Stern

(10) Patent No.: US 11,363,984 B2
(45) Date of Patent: Jun. 21, 2022

(54) METHOD AND SYSTEM FOR DIAGNOSIS AND PREDICTION OF TREATMENT EFFECTIVENESS FOR SLEEP APNEA

(71) Applicant: BLUESLEEP NY, LLC, New York, NY (US)

(72) Inventor: Jordan C. Stern, New York, NY (US)

(73) Assignee: SNOOZE, INC., New York, NY (US)

( * ) Notice: Subject to any disclaimer, the term of this patent is extended or adjusted under 35 U.S.C. 154(b) by 898 days.

(21) Appl. No.: 16/128,596

(22) Filed: Sep. 12, 2018

(65) Prior Publication Data

US 2019/0117151 A1    Apr. 25, 2019

Related U.S. Application Data

(60) Provisional application No. 62/557,470, filed on Sep. 12, 2017.

(51) Int. Cl.
| | |
|---|---|
| *A61B 5/00* | (2006.01) |
| *G16H 10/20* | (2018.01) |
| *G16H 50/20* | (2018.01) |
| *H04N 5/232* | (2006.01) |
| *G06T 7/00* | (2017.01) |
| *G06T 7/60* | (2017.01) |

(Continued)

(52) U.S. Cl.
CPC .......... *A61B 5/4818* (2013.01); *A61B 5/1079* (2013.01); *A61B 5/4848* (2013.01); *A61B 5/7275* (2013.01); *G06N 7/005* (2013.01); *G06T 7/0012* (2013.01); *G06T 7/60* (2013.01); *G16H 10/20* (2018.01); *G16H 50/20* (2018.01); *H04N 5/23222* (2013.01); *A61B 5/1072* (2013.01); *A61B 5/1116* (2013.01); *A61B 5/6898* (2013.01); *A61B 5/7246* (2013.01); *A61B 5/7264* (2013.01); *A61B 5/7465* (2013.01); *A61B 5/7475* (2013.01); *G06T 2207/20076* (2013.01); *G06T 2207/20081* (2013.01); *G06T 2207/30201* (2013.01)

(58) Field of Classification Search
None
See application file for complete search history.

(56) References Cited

U.S. PATENT DOCUMENTS

| | | |
|---|---|---|
| 9,687,193 B2 | 6/2017 | Mireshghi |
| 2014/0228905 A1* | 8/2014 | Bolea .................... A61F 5/56 607/42 |

(Continued)

OTHER PUBLICATIONS

Sanders et al., "Say ah: comparing Mallampati with and without phonation as a predictor of laryngoscopic view". 2012. The anesthesiology annual meeting. Abstract A181. (Year: 2012).*

*Primary Examiner* — Yi-Shan Yang
(74) *Attorney, Agent, or Firm* — Porzio Bromberg & Newman P.C.

(57) ABSTRACT

An automated method and system for diagnosing sleep disorders and predicting treatment effectiveness using data collected on the user using an automated application including questionnaire, facial recognition technology, and historical user and patient data. The data can be used by a diagnostic and treatment prediction algorithm to diagnose sleep disorders, for example sleep apnea, and predict treatment effectiveness. The system is an automated, self-learning algorithm capable of assessing the risk for sleep disorders and predicting treatment effectiveness.

16 Claims, 9 Drawing Sheets

(51) Int. Cl.
*G06N 7/00* (2006.01)
*A61B 5/107* (2006.01)
*A61B 5/11* (2006.01)

(56) References Cited

U.S. PATENT DOCUMENTS

| | | | |
|---|---|---|---|
| 2015/0286793 A1* | 10/2015 | Chung | G16H 50/30 705/2 |
| 2016/0005320 A1* | 1/2016 | deCharms | A61B 8/0808 434/236 |
| 2018/0005395 A1* | 1/2018 | D'Angelo | G06T 1/0007 |
| 2020/0146622 A1* | 5/2020 | Bock | G06T 7/0016 |

* cited by examiner

* Sleep coaching program is 12 weeks
* Example of Sleep Coaching program user specific directions:
  Established a bedtime and wake up time everyday - recommend 10:30-6:30
  Eliminate Screen time after 6:30
  2 caffeine drinks per day and none after 6:30
  No eating after 6:30
* BlueSleep App allows user to track progress against daily goals

|  | Monday 11.Dez | Tuesday 12.Dez | Wednesday 13.Dez | Thursday 14.Dez | Friday 15.Dez | Saturday 16.Dez | Sunday 17.Dez | Monday 18.Dez | Tuesday 19.Dez | Wednesday 20.Dez | Thursday 21.Dez | Friday 22.Dez | Saturday 23.Dez |
|---|---|---|---|---|---|---|---|---|---|---|---|---|---|
| Wake up time | 06:20 | 06:45 | 06:20 | 06:20 | | | | | | | | | |
| Bedtime | 10:25 | 10:45 | 10:25 | 10:25 | | | | | | | | | |
| Drinks | 2 | 2 | 3 | 2 | | | | | | | | | |
| Caffeine | 12:00 | 12:00 | 12:00 | 12:00 | | | | | | | | | |
| Screen time | 09:25 | 10:00 | 09:25 | 09:25 | | | | | | | | | |
| Eating after 6:30 | 06:35 | 06:20 | 06:20 | 06:20 | | | | | | | | | |

* BlueSleep telemedicine is always available to user if needed in emergency

Sleep Coaching Questinnaire

| | CONDITION | | | | |
|---|---|---|---|---|---|
| | Medical | | | Non-Medical | |
| | 1 | 2 | 3 | 4 | 5 |
| 1. First Name | | | | | |
| 2. Last Name | | | | | |
| 3. Preferred Email | | | | | |
| 4. Which of the following statements describes your sleep complaints? Check all that apply. | Quantitative | | | | |
| a) I can't fall asleep. | 0 | 2 | 1 | 2 | 2 |
| b) I can't stay asleep. | 2 | 2 | 1 | 2 | 2 |
| c) I don't feel rested when I wake up. | 2 | 2 | 1 | 2 | 2 |
| d) I feel sleepy during the day (whether I get enough sleep or not). | 2 | 2 | 2 | 2 | 2 |
| e) I tend to fall asleep very late. | 0 | 2 | 2 | 2 | 2 |
| f) I have frequent nightmares and/or recurring dreams | 1 | 0 | 2 | 2 | 0 |
| 5. If you have been diagnosed with a sleep condition, check all of the following that apply. | Qualitative | | | | |
| a) Insomnia<br>b) Sleep Apnea<br>c) Narcolepsy<br>d) Idiopathic Hypersomnia<br>e) REM Behavior Disorder<br>f) Restless Legs Syndrome<br>g) Circadian Rhythm Disorder<br>h) Shift Work Disorder<br>i) Jet Lag<br>j) Other (please specify) | | | | | |
| 6. Do you suffer from any of the following sleep problems? | Quantitative | | | | |
| a) I snore loudly. | 2 | 2 | 0 | 0 | 0 |
| b) I've been told I stop breathing, gasp for air, and/or make noise when I breathe at night. | red flag | 0 | 0 | 0 | 0 |
| c) I've been told I kick and move a lot at night | red flag | 0 | 2 | 0 | 0 |
| d) I sleepwalk, sleeptalk, and/or do other things at night (e.g. eat, drive, gamble, shop) | red flag | 0 | 2 | 0 | 0 |
| e) Sometimes I feel like I'm awake, but I can't move (i.e. I'm paralyzed but it seems like I'm awake). | red flag | 0 | 2 | 2 | 0 |
| f) I experience sudden attacks of sleep during the day (e.g. during meetings, while driving, during conversations). | red flag | 0 | 2 | 2 | 1 |

FIG. 7A

| 7. Have you experienced a recent life crisis or dramatic change (e.g. moved, changed jobs, lost a loved one)? || Quantitative ||||
|---|---|---|---|---|---|---|
| a) | Yes | 0 | red flag | 0 | 0 | 0 |
| b) | No | 0 | 0 | 0 | 0 | 0 |
| 8. Have you recently experienced weight gain? |||||||
| a) | Yes | 2 | 0 | 0 | 0 | 0 |
| b) | No | 0 | 0 | 0 | 0 | 0 |
| 9. Rate your sleep quality: (0 = Terrible, 10 = Great) || Qualitative ||||
| 10. How many hours do you sleep on weekdays? || 0 | 1* | 0 | 2* | 2* |
| 11. How many hours do you sleep on weekends? ||||||
| 12. How many times do you wake up at night? || Quantitative ||||
| a) | None | 0 | 0 | 0 | 0 | 0 |
| b) | 1-2 Times | 1 | 1 | 0 | 0 | 0 |
| c) | More than 3 Times | 2 | 2 | 0 | 0 | 0 |
| 13. How long does it take for you to fall back asleep (minutes)? |||||||
| a) | Less Than 10 Minutes | 0 | 0 | 0 | 0 | 0 |
| b) | More Than 10 Minutes | 0 | 2 | 1 | 0 | 0 |
| 14. Do you feel rested in the morning? |||||||
| | a) Never b) Sometimes c) Often d) Always ||||||
| 15. Do you feel sleepy during the day? |||||||
| a) | Yes | 2 | 2 | 2 | 2 | 2 |
| b) | No | 0 | 0 | 0 | 0 | 0 |
| 16. How many months have you had sleeping difficulties? || Qualitative ||||
| 17. Check any of the following habits that apply to you. || Quantitative ||||
| a) | I exercise within 2 hours of my target bedtime. | 0 | 0 | 0 | 1 | 0 |
| b) | I eat dinner within 2 hours of my target bedtime. | 0 | 0 | 0 | 1 | 0 |
| c) | I often use a mobile device/laptop in bed before I sleep | 0 | 0 | 0 | 1 | 0 |
| d) | I consume alcoholic beverages within 3 hours of sleeping. | 0 | 0 | 0 | 1 | 0 |

*If the difference between the user's answers to Q.10 and Q.11 is greater than 1 hour, the values apply. Otherwise, the values are zero.

FIG. 7B

| 18. Check any of the following environment factors that apply to you. | | Quantitative | | | | |
|---|---|---|---|---|---|---|
| a) | I share a bed with a partner. | 0 | 0 | 0 | 0 | 1 |
| b) | I sleep on a full size mattress or smaller | 0 | 0 | 0 | 0 | 1 |
| c) | My bedroom is not very dark when I sleep. | 0 | 0 | 0 | 0 | 1 |
| d) | My bedroom temperature fluctuates often. | 0 | 0 | 0 | 0 | 1 |
| e) | My bedroom is noisy. | 0 | 0 | 0 | 0 | 1 |
| 19. Do you have a regular sleep schedule? (i.e. Do you sleep and wake up at the same time every day?) | | | | | | |
| a) | Yes | | | | | |
| b) | No | | | | | |
| 20, Do you feel sleepy after lunch? | | | | | | |
| a) | Yes | 1 | 1 | 1 | 2 | 0 |
| b) | No | 0 | 0 | 0 | 0 | 0 |
| 21. How many caffeinated beverages do you drink a day (Coffee, Tea, Sodas, Energy Drinks)? | | | | | | |
| a) | None | | | | | |
| b) | 1 - 2 Times | | | | | |
| c) | 2 - 4 Times | | | | | |
| d) | More Than 4 Times | | | | | |
| 22. Do you drink any caffeinated beverages within 12 hours of your bedtime? | | | | | | |
| a) | Yes | 0 | 2 | 0 | 2 | 0 |
| b) | No | 0 | 0 | 0 | 0 | 0 |
| 23. How long are your naps in minutes? | | Qualitative | | | | |
| a) | I don't nap | | | | | |
| b) | 5 - 10 Times | | | | | |
| c) | 15 - 20 Times | | | | | |
| d) | 25 - 30 Times | | | | | |
| e) | More Than 30 Times | | | | | |
| 24. Do you nap on weekdays? | | Quantitative | | | | |
| a) | Yes | 2 | 2 | 2 | 0 | 0 |
| b) | No | 0 | 0 | 0 | 0 | 0 |
| 25. If you have a tracker: What activity/sleep tracker do you have? | | Qualitative | | | | |
| 26. If you have a tracker: How many hours of sleep does your tracker report you get per night? | | Qualitative | | | | |
| 27. If you have a tracker: How often are you waking up each night? | | Qualitative | | | | |
| 28. Do you have any other sleep related issues you'd like to discuss? | | Qualitative | | | | |

FIG. 7C

METHOD AND SYSTEM FOR DIAGNOSIS AND PREDICTION OF TREATMENT EFFECTIVENESS FOR SLEEP APNEA

BACKGROUND OF THE INVENTION

Field of the Invention

The present invention relates in general to sleep disorder assessment, and more particularly to, a sleep disorder diagnostic tool, data collection device, and predictor of treatment effectiveness.

Description of Related Art

Many people suffer from a sleep disorder called sleep apnea. U.S. Pat. No. 9,687,193 describes that sleep apnea may be a potentially serious sleep disorder and may include obstructive sleep apnea or central sleep apnea. The obstructive sleep apnea may occur when throat muscles relax and makes breathing difficult. In the central sleep apnea, on the other hand, the brain may stop sending proper signals to the muscles that control breathing. Sleep apnea, in particular, the obstructive sleep apnea, which is more common, may be recognized by one or more symptoms, for example, loud snoring.

Medical questionnaires have been used to diagnosis sleep apnea. The Epworth Sleepiness Scale is a list of eight situations in which users are asked to rate their tendency to fall asleep on a scale of 0 to 3. The scale is a subjective measure of a user's sleepiness.

It is desirable to provide an improved automated method and system for diagnosing sleep disorders and predicting treatment effectiveness.

SUMMARY OF THE INVENTION

The present invention relates to an automated method and system for diagnosing sleep disorders and predicting treatment effectiveness. Data can be collected on the user for example using an automated application (app) including questionnaire, facial recognition technology, and historical user and patient data. The data can be used by a diagnostic and treatment prediction algorithm to diagnose sleep disorders, for example sleep apnea, and predict treatment effectiveness. The system is an automated, self-learning algorithm capable of assessing the risk for sleep disorders and predicting treatment effectiveness. In one embodiment, the system uses questionnaires, measurements from selfie photos, and calculation of existing and accumulating data from a database of sleep patients to diagnose sleep disorders and predict treatment effectiveness. In one embodiment, the present invention is a mobile application that will allow users to receive a recommendation showing: 1) the severity of their potential sleep disorder and 2) the effectiveness of treatment using different methods. Data collected can come in the form of users answering a comprehensive questionnaire along with facial recognition technology that will take measurements of certain facial aspects using a mobile device executing the app. Weighing these factors against historical patient data, an algorithm can automate the process of providing scores including an obstructive sleep apnea (OSA) Likelihood score and Treatment Effectiveness score.

Based on the user's questionnaire answers and physiology captured in the photos, the doctor can provide a medical order for a home sleep test. After using the home sleep test device, the data can be analyzed by a physician and the physician can provide a medical prescription through the app to treat the user's sleep disorder. At any point while interacting with the application, the user can elect to have a phone, video, or text interaction with the Physician to elicit details about their diagnosis and treatment prescription.

As an alternative, or in addition to providing a medical order for a home sleep test, if the physician determines based on the user's questionnaire answers that the user indicates for poor sleep hygiene, the physician can recommend the patient use a sleep coaching program. Sleep hygiene is the recommended behavioral and environmental practice that is intended to promote better quality sleep. The sleep coaching program is a non-medical service.

Machine learning can be used with historical data of a plurality of users to improve prediction of the likelihood of a sleep disorder and effectiveness of different forms of treatment. The system of the present invention uses technology to redesign the process for diagnosing and recommending treatment of sleep disorders such as obstructive sleep apnea.

The invention will be more fully described by reference to the following drawings.

BRIEF DESCRIPTION OF THE DRAWINGS

FIG. 6 is a schematic diagram of an example of a sleep coaching program and goal tracker.

FIGS. 7A-7C are schematic diagrams which can be combined to form an example sleep coaching questionnaire.

DETAILED DESCRIPTION

Figure 1:
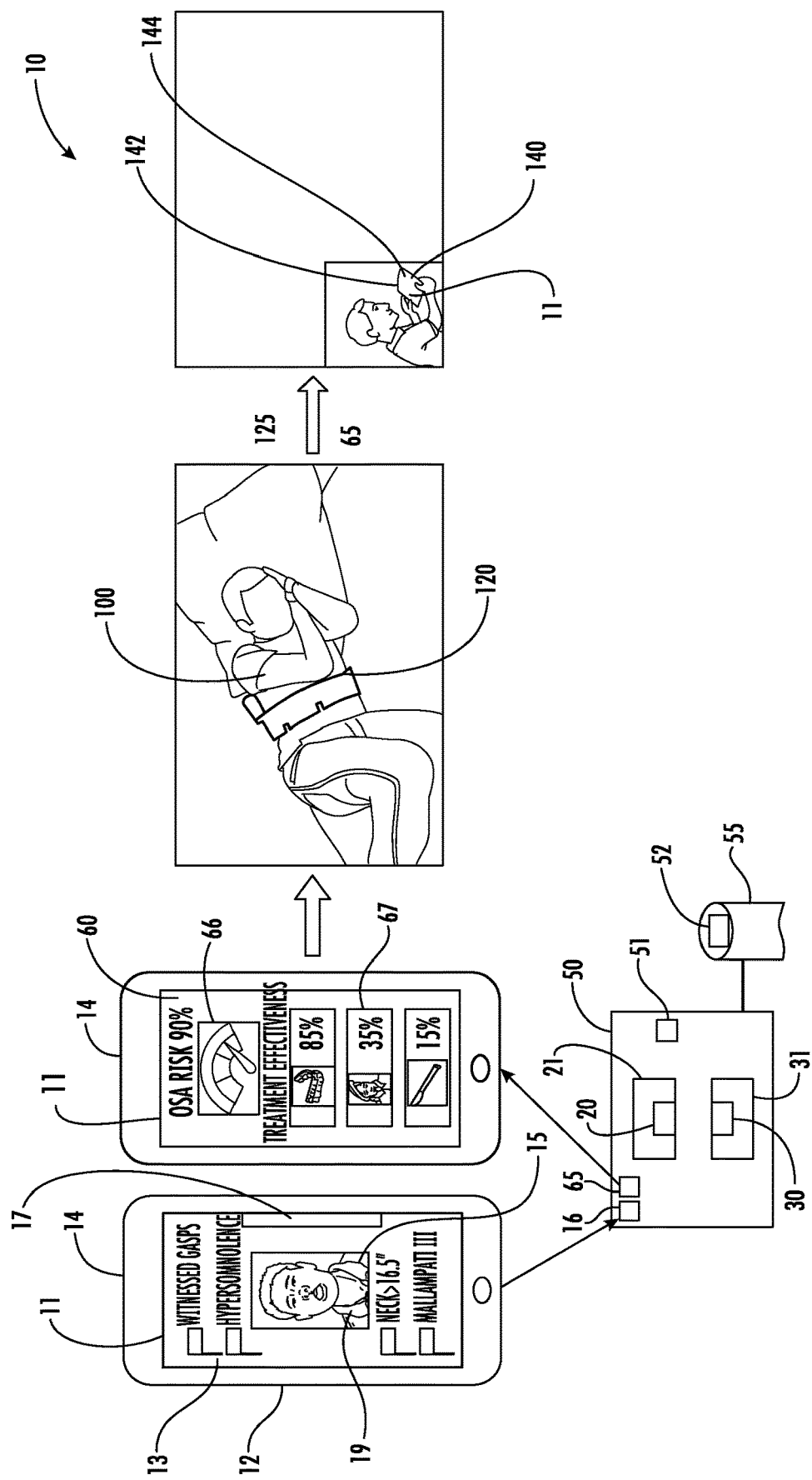
FIG. 1 is a schematic diagram of a method and system for diagnosis of sleep apnea and predicting treatment effectiveness in accordance with the teachings of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

Referring now to the drawings, FIG. 1 illustrates a flow diagram of a method and System for Diagnosis and Prediction of Treatment Effectiveness for Sleep Disorders 10. Input source 12 receives user information. For example, input source 12 can be questionnaire 13. Questionnaire 13 can be accessed using app 11 running on mobile device 14 or online for entering user data. Mobile device 14 for example can be a smart mobile telephone (smartphone) or tablet computer, Personal Data Assistant (PDA), laptop computer, and e-book reader, currently capable of loading apps which, in combination with an Internet connection can be designed to receive and display to the mobile device various data input screens for inputting information from input source 12. The user typically may select or otherwise interact with app 11, for example by clicking or touching, resulting in a resulting action such as opening questionnaire 13. App 11 can include, in the executable code 17 that constitutes app 11.

An example questionnaire 13 can include the following questions:
1. What is your height (in feet and inches)?
2. What is your weight (in pounds)? (calculate BMI)
3. How many hours do you sleep each night?
4. Do you snore?
5. Do you wake up gasping for air, short of breath, or gagging?
6. How many times do you wake up while sleeping at night?
7. Do you suffer from memory and/or concentration problems?
8. Do you complain of lack of sexual interest or decreased libido, impotence, or erectile dysfunction?
9. Are sleepy or tired during the day?
10. How often do you nap?

Input source 12 can be photograph input 15. Photograph input 15 can be received by camera app 19 running on mobile device 14. Camera app 19 can be part of app 11 or separate from app 11. Data 16 from input source 12 including results of questionnaire 13 and photograph input 15 can be used in algorithms for determining a user's OSA Likelihood score 20 and Treatment Effectiveness score 30. The algorithms can be executed on website server 50 remotely connected to input source 12. Website server 50 can include processor 51 and relational database 52. In one embodiment according to the present invention, app 11 can use questionnaire 13 to collect data in real time on XML forms, which automatically populate database 52 using a computer software application.

Dashboard 60 can display result data 65 at mobile device 14 using app 11. For example, result data 65 can be a OSA Likelihood score and Treatment Effectiveness score. User 100 can perform a sleep test using sleep monitoring device 120. Sleep monitoring device 120 can perform sleep monitoring and sleep tracking functions. For example, the sleep test can be a home monitoring sleep test. An example sleep monitoring device 120 is ApneaLink™ air home sleep testing device manufactured by Resmed Corp, San Diego, Calif. Data 125 from sleep monitoring device 120 and result data 65 can be analyzed by a physician using app 11 at device 140. Device 140 for example can be a smartphone, tablet computer, laptop computer, or desktop computer equipped with camera 142 and microphone 144. The physician can provide a medical prescription through app 11 at device 140 to treat the user's sleep disorder.

The method of the present invention can include the following steps:
1. The user downloads app 11 and registers at mobile device 14
2. The user begins inputting data into questionnaire 13 using app 11 executing on mobile device 14
3. The user is asked to enter photograph input 14, such as for example to complete several selfie type photos, in app 11 using camera app 19 to capture physiology. App 11 instructs the user via text and/or voice which photos need to be taken and from what angles with camera app 19 to enable the required measurements
4. App 11 uses facial recognition to translate photograph input 14 to measurements
5. OSA Likelihood algorithm 21 and Treatment Effectiveness algorithm 31 calculate scores using results of questionnaire 13, facial recognition measurements measured with camera app 19, and historical patient data 55
6. Scores are presented to the user in app 11
7. The user has an option to set up telemedicine consultation with a sleep doctor via app 11.

Figure 2:
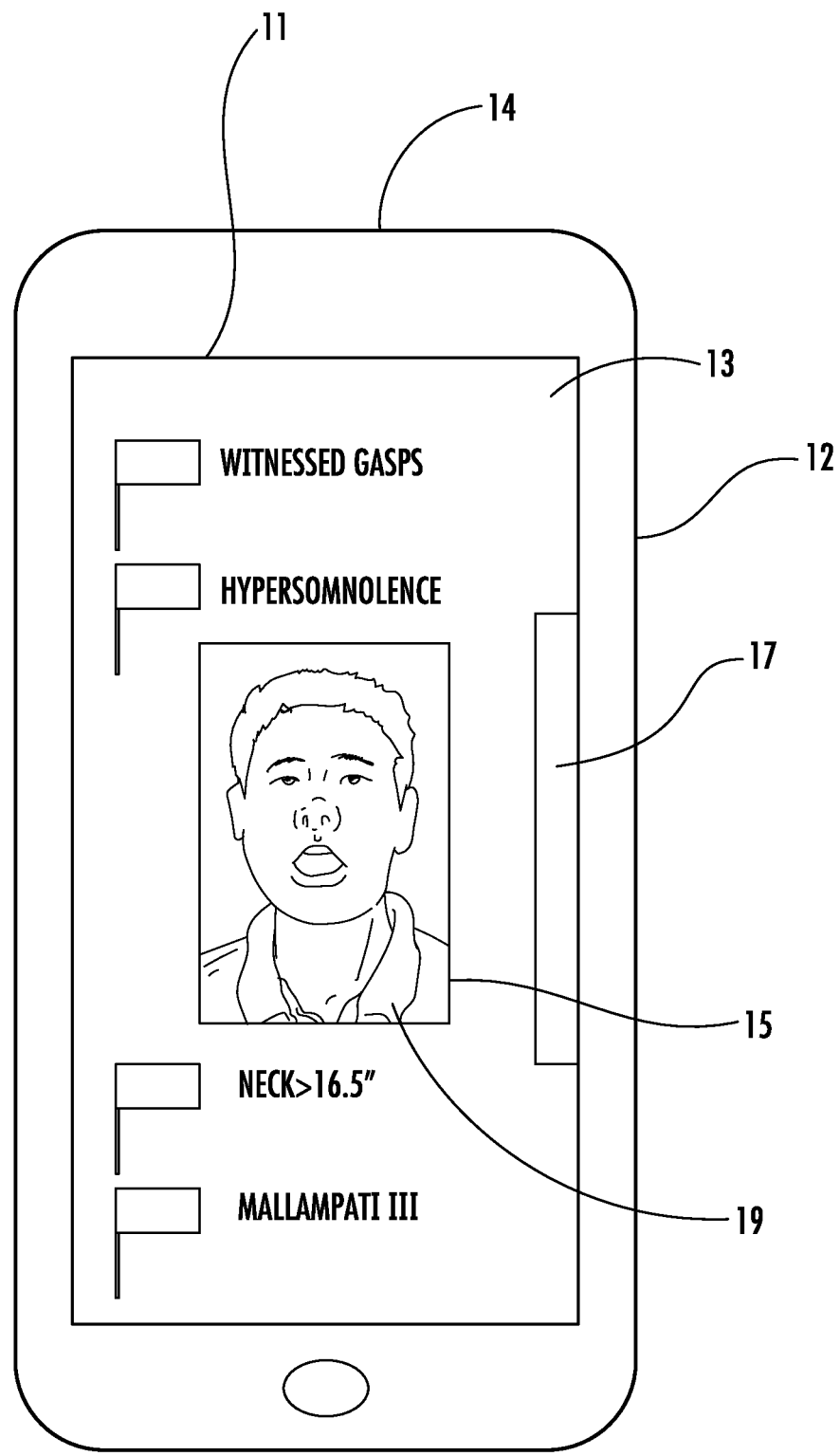
FIG. 2 is a schematic diagram of screen shot of an app running on a mobile device used in the implementation of the present invention for collection of data.

For collection of photograph input 15, app 11 can instruct the user to hold mobile device 14 at certain angles to take specific selfie photographs or their face and neck using camera app 19 as shown in FIG. 2. App 11 can guide the user so their face fits within the selfie facial frame. Photograph input 15 can be used in facial recognition technology to detect the measurement of facial features which is valuable in helping determine if the user has a sleep disorder, such as sleep apnea.

The method for collection of photograph input can include the following steps:
1. Take a photo of your face straight ahead
   a. Measures length and width of face
2. Take a profile picture in app 11
   a. measures angle between neck and chin in app 11
3. Say ahh and stick your tongue out and take a photo
   a. Measures Mallampati score in app 11
4. Look up and take a picture of your neck
   a. Measures neck circumference in app 11
5. Look up and take a picture of your nostrils
   a. Measures septal deviation and airflow in app 11

Historical patient data 55 included in relational database 52 can be compared against the current user's measurements determined from input source 12 to calculate OSA Likelihood score 20 using OSA Likelihood algorithm 21 and Treatment Effectiveness score 30 using Treatment Effectiveness algorithm 31. OSA Likelihood algorithm 21 automates the interpretation of data from relational database 52 and a rules engine to automatically create OSA Likelihood score 20. Treatment Effectiveness algorithm 31 automates the interpretation of data from relational database 52 and a rules engine to automatically create Treatment Effectiveness score 30.

Example measurements of historical patient data 55 can include:
Height; Weight; Age; Gender; BMI; Neck circumference; Intraoral photo and score; Treatment type; Treatment efficacy; Epworth score (modified); Snore Severity score; Associated medical conditions (especially: hypertension, heart disease, diabetes); History of tonsillectomy; History of nasal sinus surgery and the like.

OSA Likelihood algorithm 21 can be used to calculate OSA Likelihood score 20 for a user. The components of OSA Likelihood algorithm 21 can include responses from questionnaire 13, facial recognition measurements from photograph input 15, and relative similarity to historical patient data 55.

A suitable weighting of OSA Likelihood algorithm 21 is:

[OSA Likelihood Score]=[0.33*Questionnaire]+
 [0.33*Facial Measurements]+[0.33*Historical
 Patient Similarity]

Treatment Effectiveness algorithm 31 can be used to calculate the Treatment Effectiveness score 30 for a user. The components of Treatment Effectiveness algorithm 31 can include responses from questionnaire 13, facial recognition measurements from photograph input 15, and relative similarity to historical patient data 55.

OSA Likelihood score 20 using OSA Likelihood algorithm 21 and Treatment Effectiveness score 30 using Treatment Effectiveness algorithm 31 using App 11 content information and matching the app information obtained from the lookup is then classified. The classification may include statistical machine-learning to analyze the app information for its content. Any classification method that uses supervised learning, unsupervised learning, reinforcement learning, direct string matching, etc. on a processor may be used to classify the app content according to predefined parameters. Although not illustrated, it is appreciated that multiple classifications may be performed in parallel, such as by use of parallel processing or by multiple app classification controllers each acting on a predetermined subset of records in the app information cache. Scores can be shown in graphic 67 for each type of available treatment.

Available treatments include:

Oral appliance therapy (OAT); Continuous positive airway pressure (CPAP); Surgery and the like.

Suitable weighting of Treatment Effectiveness algorithm 31 is:

[Treatment Effectiveness Score]=[0.33*Questionnaire]+[0.33*Facial Measurements]+[0.33*Historical Patient Similarity]

Figure 3:
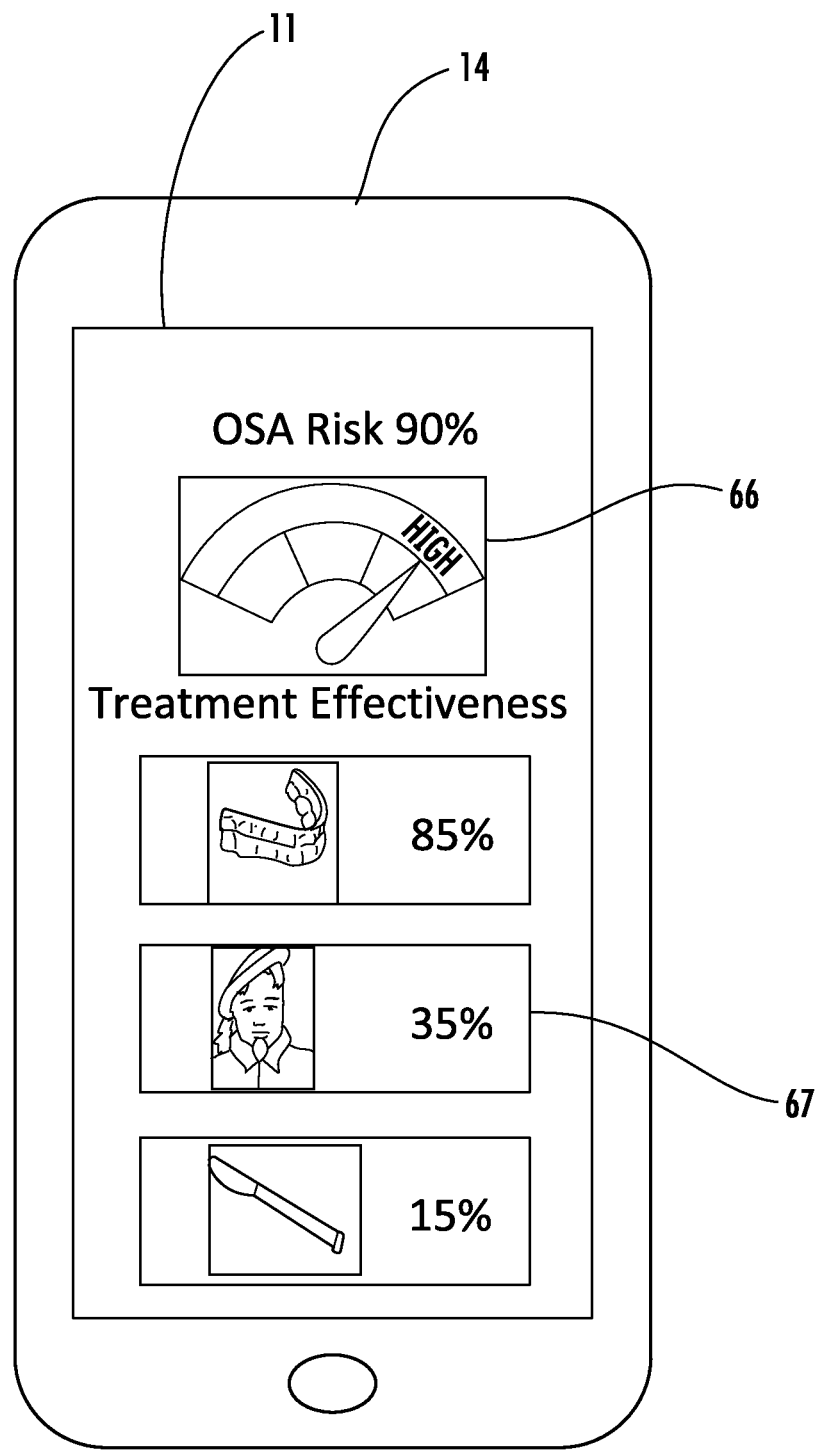
FIG. 3 is a schematic diagram of screen shot of an app running on a mobile device used in the implementation of the present invention for displaying results.

Dashboard 60 can display graphic 66 of OSA Risk determined from OSA Likelihood score 20 as shown in FIG. 3. Dashboard 60 can display graphic 67 of Treatment Effectiveness Score 30.

All user's facial measurements from photograph input 15 and questionnaire 13 answers are collected by app 11. These will be added to database 52 that includes past patient data. The data collected over time will be used to evaluate the correlation of facial data with the actual diagnosis and severity of the sleep disorder, such as for example sleep apnea, predicted by app 11, as well as the user's response to treatment, if applicable. As more people use app 11, more data is accumulated, improving the correlation of facial characteristics and questionnaire responses to the actual existence of the sleep disorder, the severity of sleep disorder, and the response to treatment if applicable. As the number of users increases the algorithm, using machine learning, will become more accurate, and more precisely inform users of their risk of a sleep disorder, such as for example sleep apnea, and their likely response to treatment.

Figure 4:
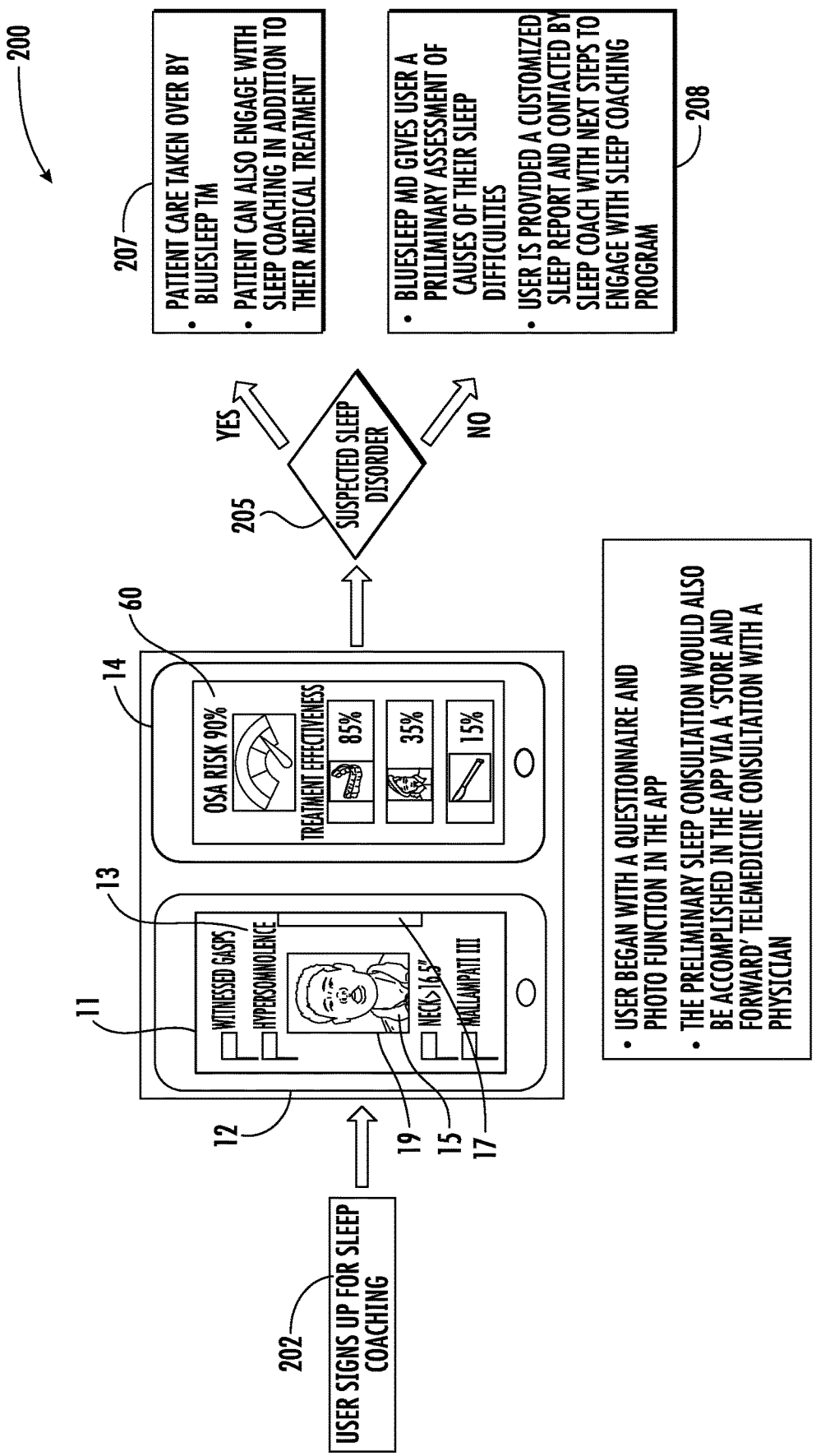
FIG. 4 is a schematic diagram of a method and system for separating medical and non-medical users for diagnosis of sleep disorders and predicting treatment effectiveness in accordance with the teachings of the present invention.

FIG. 4 is a schematic diagram of a method and system for separating medical and non-medical users 200 which can be used in combination with the diagnosis of sleep disorders and predicting treatment effectiveness in accordance with the teachings of the present invention described above. In block 202, a user registers for sleep coaching with app 11. All user's facial measurements from photograph input 15 and questionnaire 13 answers are collected by app 11. Results of questionnaire 13 and photograph input 15 can be used in algorithms for determining a user's OSA Likelihood score 20 and Treatment Effectiveness score 30 as described above.

Dashboard 60 can display results 65 at mobile device 14 using app 11. For example, results 65 can be a OSA Likelihood score and Treatment Effectiveness score. Based on user's questionnaire answers a suspected sleep disorder decision is made in block 205. A preliminary sleep consultation can be performed in app 11 such as with a store and forward telemedicine consultation with a physician in order to make the decision in block 205. If a sleep disorder is determined in block 205, in block 207 the method and System for Diagnosis and Prediction of Treatment Effectiveness for Sleep Disorders 10 can be performed for the medical user. If a sleep disorder is not determined in block 206, in block 208 a sleep coaching assessment process can be performed.

Figure 5:
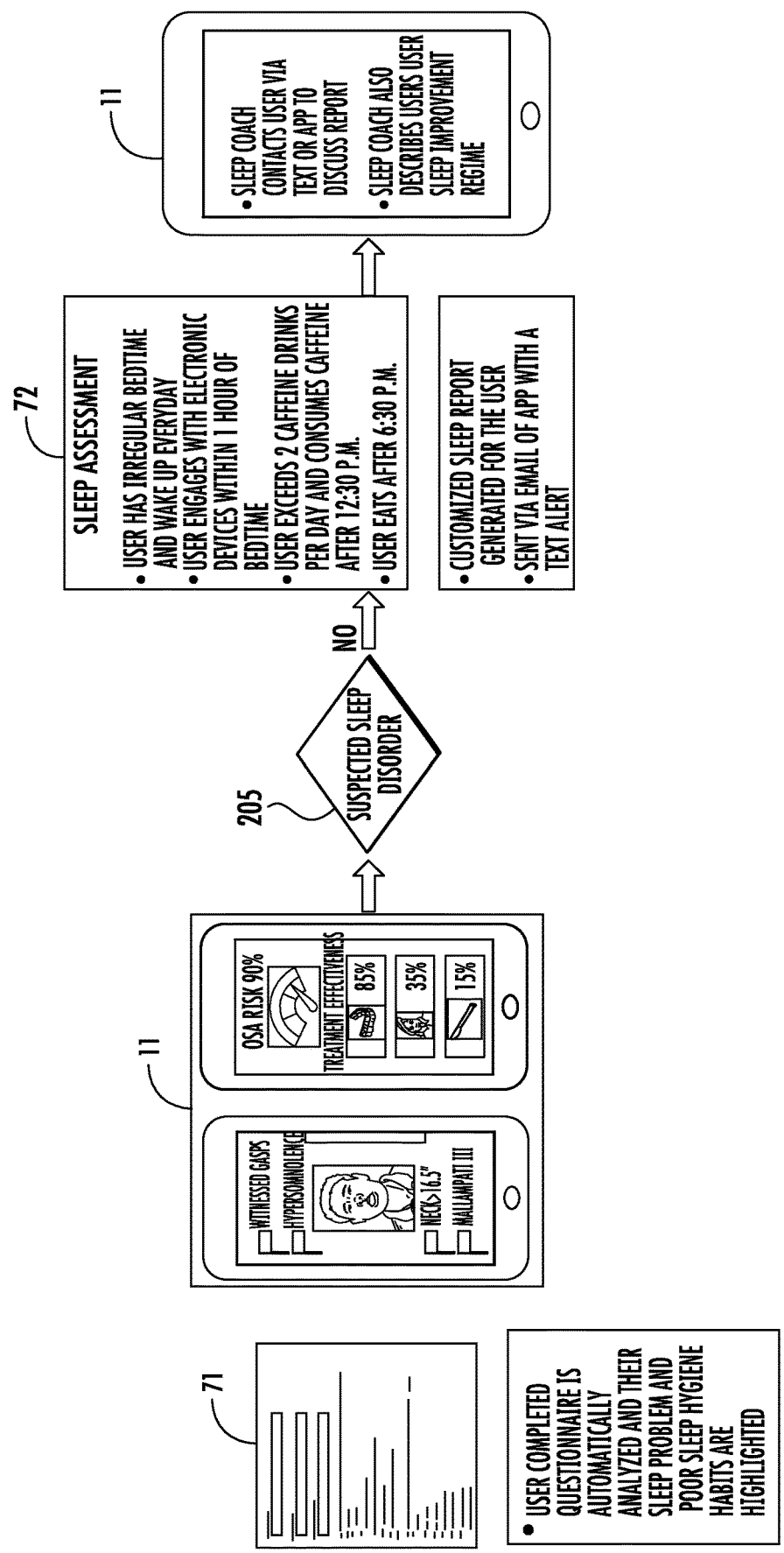
FIG. 5 is a s schematic diagram of a system for implementing a sleep coaching program.

FIG. 5 illustrates system for implementing a sleep coaching program 201. Questionnaire 71 is inputted into app 11. A sleep coaching assessment process performed by app 11 can create sleep report 72. Sleep report 72 can identify the user's poor sleep hygiene behaviors, provide explanations as to why these behaviors are interfering with sleep, and instructions for how the user can improve these habits. Sleep report 72 can be delivered in app 11. A copy of sleep report 72 can be sent via email to the user. Within a pre-determined time, such as for example 12 hours, of sleep report 72 being sent, the user is contacted via text and alert notification in app 11 by a sleep coach who engages with the user in a text or via app 11 with a note interaction to answer the user's questions regarding sleep report 72.

Based on the user's questionnaire answers, in addition to report 72, the automated sleep coaching assessment can generate a time based sleep coaching program 73, such as a 12 week program for the user as shown in FIG. 6. Sleep coaching program 73 provides the user specific program goals 74 intended to correct the user's poor sleep hygiene. The program goals 74 can be daily goals. App 11 can provides an interactive tracker which delivers the user's daily goals and allows the user to input their actual data. App 11 can automatically flag missed goals 75 and also notify the user's assigned sleep coach who can communicate with the user via text or in app 11, such as with notes.

Sleep coaching program 73 can use variable and random rewards including coupons and free services to engage the user. The user's performance against their respective program goals 74 will also be compared to anonymized data from other user's, and the user's relative performance and rank can be made visible to the user to elicit competitive motivation and better adherence to program goals.

The user's sleep coach can periodically communicate via text or via in app 11, such as with notes, for example, at least once a week to allow the user the opportunity to ask questions and discuss their performance. User initiated interactions can be limited in time, such as to twice a week. User interactions with their coach can have a word limit for example of 50 words per interaction.

An Example questionnaire includes 25 sleep-related questions: 14 quantitative and 11 qualitative as shown in the combination of FIGS. 7A-7C.

Qualitative Analysis:

The qualitative responses are used to:

1) Pinpoint non-quantifiable behavioral and/or environmental flaws that could potentially contribute to the user's sleep problems
2) Support the results of the quantitative analysis
3) Prepare the user's on-going sleep diary (i.e. aspects to improve) for Sleep Coaching Quantitative Analysis:

The quantitative questions are used to calculate the theoretical risk of each condition The conditions (i) are:

| i | Classification | Condition |
|---|---|---|
| 1 | Medical | Obstructive Sleep Apnea (OSA) |
| 2 | Medical | Insomnia |
| 3 | Medical | Disorder - Other |
| 4 | Non-Medical | Behavioral |
| 5 | Non-Medical | Environmental |

The following equation can be used for quantitative analysis:

$$C_i = \frac{\sum Q_i}{Q_{i_{max}}} \times 100$$

$i$ = Condition (medical or non-medical)

$C_i$ = Theoretical risk of '$i$'

$Q_i$ = Responses corresponding to '$i$'

$Q_{imax}$ = Maximum response value corresponding to '$i$'

The equation calculates the theoretical chance of the presence of each condition based on the user's responses from the sleep questionnaire 71. Each quantitative question is assigned a value of 0, 1, or 2. These values are assigned based on prior patient study data, published research, and physician's expertise and experience.

The risk factor is divided into 3 zones and the user is presented with a visual for each condition:

| Zone | $C_i$ (%) | Assessment |
| --- | --- | --- |
| Red | 67 to 100 | High Chance |
| Yellow | 33 to 67 | Medium Chance |
| Green | 0 to 33 | Low Chance |

In one embodiment, "red flag" responses can be automatically move the user to the red zone for that particular condition, regardless of other responses.

It should be understood that any of the method steps and calculations described herein may be performed on a special purpose computer, such as a general purpose computer programmed with software and/or hardware, having embedded therein instructions for the computer to perform the specified steps. Furthermore, any displays depicted herein may be generated by a computer connected to and accessible via a computer network, such as but not limited to the Internet or World Wide Web, and may be generated in response to a user or healthcare provider accessing the computer through the computer network and providing identification, such as a secure username and password, that permits access to the information. The invention is not limited to the use of any particular display format, computer language, or type of network, and those of skill in the art of computer design and programming will find sufficient information disclosed herein, and in the provisional application incorporated herein by reference, to facilitate the disclosed functionalities.

Embodiments of the present invention may be implemented in connection with a special purpose or general purpose telecommunications device that include both hardware and/or software components, including wireless telephones and other telephony-enabled wireless devices, landline telephones, or special purpose or general purpose computers that are adapted to have telecommunications capabilities.

Embodiments may also include physical computer-readable media and/or intangible computer-readable media for carrying or having computer-executable instructions, data structures, and/or data signals stored thereon. Such physical computer-readable media and/or intangible computer-readable media can be any available media that can be accessed by a general purpose or special purpose computer. By way of example, and not limitation, such physical computer-readable media can include RAM, ROM, EEPROM, CD-ROM or other optical disk storage, magnetic disk storage or other magnetic storage devices, other semiconductor storage media, or any other physical medium which can be used to store desired data in the form of computer-executable instructions, data structures and/or data signals, and which can be accessed by a general purpose or special purpose computer. Within a general purpose or special purpose computer, intangible computer-readable media can include electromagnetic means for conveying a data signal from one part of the computer to another, such as through circuitry residing in the computer.

When information is transferred or provided over a network or another communications connection (either hardwired, wireless, or a combination of hardwired or wireless) to a computer, hardwired devices for sending and receiving computer-executable instructions, data structures, and/or data signals (e.g., wires, cables, optical fibers, electronic circuitry, chemical, and the like) should properly be viewed as physical computer-readable mediums while wireless carriers or wireless mediums for sending and/or receiving computer-executable instructions, data structures, and/or data signals (e.g., radio communications, satellite communications, infrared communications, and the like) should properly be viewed as intangible computer-readable mediums. Combinations of the above should also be included within the scope of computer-readable media.

Computer-executable instructions include, for example, instructions, data, and/or data signals which cause a general purpose computer, special purpose computer, or special purpose processing device to perform a certain function or group of functions. Although not required, aspects of the invention have been described herein in the general context of computer-executable instructions, such as program modules, being executed by computers, in network environments and/or non-network environments. Generally, program modules include routines, programs, objects, components, and content structures that perform particular tasks or implement particular abstract content types. Computer-executable instructions, associated content structures, and program modules represent examples of program code for executing aspects of the methods disclosed herein.

Embodiments may also include computer program products for use in the systems of the present invention, the computer program product having a physical computer-readable medium having computer readable program code stored thereon, the computer readable program code comprising computer executable instructions that, when executed by a processor, cause the system to perform the methods of the present invention. For example, in an embodiment, the invention provides a program product stored on a computer-readable medium, which when executed, enables a computer infrastructure to establish an interface for inputting sleep data and providing an automated sleep assessment which can include an obstructive sleep apnea (OSA) Likelihood score and Treatment Effectiveness score (FIG. 1), which implements the process described herein. It is understood that the term "computer-readable medium" comprises one or more of any type of physical embodiment of the program code. In particular, the computer-readable medium can comprise program code embodied on one or more portable storage articles of manufacture (e.g., a compact disc, a magnetic disk, a tape, etc.), on one or more data storage portions of a computing device, and/or as a data signal traveling over a network (e.g., during a wired/wireless electronic distribution of the program product).

There is little distinction left between hardware and software implementations of aspects of systems; the use of hardware or software is generally (but not always, in that in certain contexts the choice between hardware and software can become significant) a design choice representing cost versus efficiency trade-offs. There are various vehicles by which processes and/or systems and/or other technologies described herein can be effected (e.g., hardware, software, and/or firmware), and the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation. In one or more other scenarios, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof.

In one or more embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments described herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof. Those skilled in the art will further recognize that designing the circuitry and/or writing the code for the software and/or firmware would be well within the skill of one of skilled in the art in light of the present disclosure.

Additionally, those of ordinary skill in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable-type medium such as a floppy disk, a hard disk drive, a Compact Disc (CD), a Digital Video Disk (DVD), a digital tape, a computer memory, etc.; and a transmission-type medium such as a digital and/or an analog communication medium (e.g., a fiber optic cable, a waveguide, a wired communications link, a wireless communication link, etc.).

Those of ordinary skill in the art will also recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having ordinary skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed:

1. A method for diagnosis for sleep disorders and prediction of treatment effectiveness for the sleep disorders, comprising:
   obtaining user information of an user from an input source by a camera application executing on a mobile device, wherein the input source comprises photograph input of a face and/or a neck of the user received by the camera application executing on the mobile device, wherein the camera application instructs the user to hold the mobile device at certain angles of the face and/or the neck of the user using the camera application for generating the photograph input of the face and/or the neck of the user, and the camera application measures one or more features of the photograph input;
   storing the obtained user information in a storage medium;
   analyzing the stored user information to determine an obstructive sleep apnea (OSA) likelihood score and a treatment effectiveness score for the diagnosis of the sleep disorders and the prediction of the treatment effectiveness for the sleep disorders; and
   presenting the obstructive sleep apnea (OSA) likelihood score and the treatment effectiveness score at the mobile device with the camera application.

2. The method of claim 1, wherein the input source further comprises a questionnaire.

3. The method of claim 1, the application instructs to user to perform one or more of the actions from the group consisting of: to face straight ahead during the use of the camera application and the application measures a length and width of the face; to take a profile photograph during the use of the camera application and the application measures an angle between the neck and a chin of the user; to say ahh and stick out a tongue of the user during the use of the camera application and the application measures a Mallampati score; to look up and take a photograph of the neck of the user with the camera application and the application measures a neck circumference of the user; and to look up and take a photograph of nostrils of the user during the use of the camera application and the application measures a septal deviation and airflow of the user.

4. The method of claim 1 further comprising a step of: storing historical patient data in a remote server and using the stored historical patient data in the step of analyzing the stored user information to determine the obstructive sleep apnea (OSA) likelihood score and the treatment effectiveness score.

5. The method of claim 4, wherein the input source further comprises a questionnaire which collects the user information in real time and automatically populates a database of the remote server.

6. The method of claim 5, wherein statistical machine learning techniques are used to perform determination of the obstructive sleep apnea (OSA) likelihood score and the treatment effectiveness score.

7. The method of claim 1, wherein a dashboard display results of the obstructive sleep apnea (OSA) likelihood score and the treatment effectiveness score at the mobile device with the application.

8. The method of claim 1, wherein a suspected sleep disorder decision is made based on the obstructive sleep apnea (OSA) likelihood score and the treatment effectiveness score and a preliminary sleep consultation is performed and forwarded to a physician.

9. The method of claim 1 further comprising a step of: providing a sleep coaching assessment process performed by the application to create a sleep report to identify sleeping habits.

10. A system for diagnosis for sleep disorders and prediction of treatment effectiveness for the sleep disorders, comprising:
  a processor; and
  a non-transitory memory storage system in data communication with the processor and including instructions executable by the processor and that upon such execution case the processor to perform operations comprising:
    obtaining user information of a user from an input source by a camera application executing on a mobile device,
      wherein the input source comprises photograph input of a face and/or a neck of the user receive by the camera application executing on the mobile device,
      wherein the camera application instructs the user to hold the mobile device at certain angles of the face and/or the neck of the user using the camera application for generating the photograph input, and the camera application measures one or more features of the photograph input;
    storing the obtained user information in a storage medium;
    analyzing the stored user information to determine an obstructive sleep apnea (OSA) likelihood score and a treatment effectiveness score to the user for the diagnosis of the sleep disorders and the prediction of the treatment effectiveness for the sleep disorders; and
    presenting the obstructive sleep apnea (OSA) likelihood score and the treatment effectiveness score at the mobile device with the camera application.

11. The system of claim 10, wherein the input source further comprises a questionnaire.

12. The system of claim 10, wherein the application instructs to user to perform one or more of the actions from the group consisting of: to face straight ahead during the use of the camera application and the application measures a length and width of the face; to take a profile photograph during the use of the camera application and the application measures an angle between the neck and a chin of the user; to say ahh and stick out a tongue of the user during the use of the camera application and the application measures a Mallampati score; to look up and take a photograph of the neck of the user with the camera application and the application measures a neck circumference of the user; and to look up and take a photograph of nostrils of the user during the use of the camera application and the application measures a septal deviation and airflow of the user.

13. The system of claim 10, wherein the operations further comprising storing historical patient data in a remote server and using the stored historical patient data in the step of analyzing the stored user information to determine the obstructive sleep apnea (OSA) likelihood score and the treatment effectiveness score.

14. The system of claim 13, wherein the input source further comprises a questionnaire which collects the user information in real time and automatically populates a database of the remote server.

15. A non-transitory memory storage system storing instructions executable by a processor and that upon such execution cause the processor to perform operations for diagnosis for sleep disorders and prediction of treatment effectiveness for the sleep disorders, comprising:
  obtaining user information of an user from an input source by a camera application executing on a mobile device,
    wherein the input source comprises photograph input of a face and/or a neck of the user received by the camera application executing on the mobile device and
    wherein the camera application instructs the user to hold the mobile device at certain angles of the face and/or the neck of the user using the camera application for generating the photograph input and the application measures one or more features of the photograph input
  storing the obtained user information in a storage medium;
  analyzing the stored user information to determine an obstructive sleep apnea (OSA) likelihood score and a treatment effectiveness score for the diagnosis of the sleep disorders and the prediction of the treatment effectiveness for the sleep disorders; and
  presenting the obstructive sleep apnea (OSA) likelihood score and the treatment effectiveness score at the mobile device with the camera application.

16. The non-transitory memory storage system method of claim 15, wherein the input source further comprises a questionnaire.

* * * * *